United States Patent [19]

Pinnavaia et al.

[11] Patent Number: 4,605,621

[45] Date of Patent: Aug. 12, 1986

[54] CLAY-ENZYME COMPLEXES AND METHOD FOR PREPARING SAME

[75] Inventors: Thomas J. Pinnavaia; Max M. Mortland; Stephen A. Boyd, all of East Lansing, Mich.

[73] Assignee: Michigan State University, East Lansing, Mich.

[21] Appl. No.: 676,171

[22] Filed: Nov. 29, 1984

[51] Int. Cl.[4] .............................................. C12N 11/02
[52] U.S. Cl. .................................... 435/177; 435/176; 435/190; 435/200; 435/207
[58] Field of Search ............... 435/176, 177, 190, 200, 435/207

[56] References Cited

U.S. PATENT DOCUMENTS

| | | | |
|---|---|---|---|
| 2,531,396 | 11/1950 | Carter et al. | 106/308 N X |
| 3,974,125 | 8/1976 | Oswald et al. | 523/521 X |
| 4,081,496 | 3/1978 | Finlayson | 523/521 X |
| 4,367,163 | 1/1983 | Pinnavaia et al. | 252/80 |
| 4,430,348 | 2/1984 | Duncombe et al. | 435/176 X |
| 4,504,582 | 3/1985 | Swann | 435/177 X |
| 4,522,924 | 6/1985 | Tennent et al. | 435/176 X |

FOREIGN PATENT DOCUMENTS 2128620  5/1984  United Kingdom ............... 435/177

OTHER PUBLICATIONS

Pinnavaia, American Chemical Society Symposium Series, No. 192 (1982), 241–253.

*Primary Examiner*—Howard E. Schain
*Attorney, Agent, or Firm*—Stefan J. Klauber

[57] ABSTRACT

Immobilized enzymes are prepared by reacting an enzyme to be immobilized with an organoclay. The immobilized enzymes are enzyme-organoclay complexes in which the binding is substantially pH independent.

14 Claims, No Drawings

CLAY-ENZYME COMPLEXES AND METHOD FOR PREPARING SAME

FIELD OF THE INVENTION

The present invention relates generally to novel clay-enzyme compositions, and more specifically relates to novel organoclay-enzyme complexes, wherein the enzymes are immobilized but the activity thereof is not exclusively inhibited. The invention further relates to a method of preparing the aforementioned complexes.

BACKGROUND OF THE INVENTION

The use of enzymes in industrial applications, and for various biological and medical purposes is well-known. Such materials find use e.g. in the construction of membranes for enzyme therapy, as in artificial kidneys and other artificial organs. They are also used in conjunction with electrodes and related detection devices for medical diagnostics, and as catalysts in enzyme reactors, etc. These and other enzyme uses have been growing rapidly as the availability thereof increases and the unique catalytic characteristics of these materials are better understood.

In general, the limited availability of the various enzymes and attendant high costs have been a serious detriment to their wider use in commercial applications. The use of free enzymes in aqueous compositions is simply not economically feasible because of the excessive loss of the enzyme that results and the difficulty in controlling the amount, activity and stability thereof in such an environment.

As is well known, one of the most advantageous techniques that has been found for making feasible the practical use of enzymes, involves immobilization of enzymes on substrates that serve to confer stability to the enzymes. In such cases, the enzyme is absorbed or absorbed on a substrate in such a manner that a sufficient amount of the enzyme is available for the projected use, and the activity, generally catalytic activity, is not unduly limited by the immobilization mechanism.

Previous approaches to the immobilization of enzymes have employed coupling agents to covalently link the enzyme to the support surface. Typical functionalized supports have included porous and non-porous glass, nickel oxide, silicaalumina, polyacrylamide, polystyrene, albumin and cellulose. Other approaches have physically incorporated the enzyme into porous matrices such as cellophane, controlled pore titania, collagen, silicone elastomers and polyacrylamide gel. The specific activity and stability of an enzyme immobilized by covalent attachment or occlusion depends strongly on the nature of the support and on a variety of operational factors which generally influence the performance of immobilized enzymes, such as the pH and/or temperature stability profile of the bound enzyme.

It has also been recognized for a number of years that swelling smectite clay minerals such as sodium-montmorillonite and hectorite, bind enzymes by an ionic intercalation mechanism, often with retention of catalytic activity. Enzyme immobilization on sodium exchanged or unmodified layered clays has been found to be extremely pH dependent. Below the enzyme isoelectric point, strong interactions for enzyme immobilization are provided. However, above the isoelectric point, where the enzyme become negatively charged, the enzymes are readily desorbed from the clay surface. This behavior is undesirable because the pH for optimum enzyme activity is often above the isoelectric point. Further, enzymes bound to unmodified clays exhibit substantially reduced activity relative to homogeneous solutions and are readily denatured.

More recent studies of alternate routes to enzyme immobilization have recognized a potential significance of hydrophobic binding mechanisms for influencing the efficiency of immobilized enzymes. Such studies, however, have generally been limited in scope and the effect of factors that may relate to such mechanisms are not known.

Organic-clay complexes, which are the reaction products of smectite-type clay minerals as well as certain synthetic material resembling them, are well known and have been widely used as gelling and viscosity control agents for organic liquids such as lubricating oils, linseed oil, toluene and the like. A large variety of highly useful products, such as lubricating greases are produced through use of such gelling agents. The procedures and chemical reactions pursuant to which these organoclays are prepared are also well known.

Among the prior art patents which discuss at length aspects of the preparation and properties of organicclay complexes (organoclays) are U.S. Pat. Nos. 2,531,396; 2,531,427; 2,531,440; 2,966,506; 3,227,657; 3,298,849; 3,422,185; 3,537,994; 3,974,125; and 4,081,496, and U.K. Pat. No. 920,797. Reference may also be made to applicable portions of the standard reference by Ralph E. Grim, "Clay Mineralogy", 2d Edition, 1968, McGraw Hill Book Company. None of these references nor other disclosures in the prior art have been addressed to or have suggested providing an immobilized enzyme composition or of any means for immobilizing enzymes.

It is evident that there are limitations in the mechanisms that are known for immobilizing enzymes including pH dependence, ready denaturation, inhibited catalytic activity, excessive cost of materials and/or complexity of synthesizing techniques. It would, therefore, be highly desirable to prepare immobilized enzymes which were catalytically active over the broadest possible pH and temperature ranges and would lend itself to the least complex synthetic methodology.

It is, therefore, a primary object of this invention to provide a method for immobilizing enzymes by mechanisms which are substantially pH-independent.

Another object of this invention is to provide new and improved immobilized enzyme compositions.

Still another object of this invention is to provide a method for the pH-independent immobilization of enzymes which is simple to carry out and which employs readily available binding materials for said enzymes.

Yet another object of this invention is to provide new and improved immobilized enzymes which, depending on the nature of the enzyme and on the nature of the immobilizing component, may completely inhibit the activity of the immobilized enzyme, or may exhibit activity substantially comparable to the activity of the free enzyme in homogeneous solution, or may be modified to some other degree of activity.

Another object of this invention is to provide a method for producing immobilized enzyme-organoclay complexes in which enzyme binding is substantially independent of solution pH.

Still another object of this invention is to provide new and improved enzyme-organoclay complexes in which the enzymes are immobilized and in which the binding is substantially independent of solution pH.

Yet another object of this invention is to provide enzyme-organoclay complexes having loadings of immobilized enzymes up to about 40 percent by weight or even greater.

These and still further objects of the invention will become readily apparent to one skilled in the art from the following detailed description, specific examples and drawings.

SUMMARY OF THE INVENTION

In accordance with the present invention, there is provided a process for preparing immobilized enzymes which comprises reacting an enzyme to be immobilized with an organoclay.

It has been discovered that immobilized enzymes can be readily prepared by the reaction of a mixture of an organoclay and an enzyme which is independent of the solution pH. Depending on the nature of the enzyme and the nature of the clay complex, the catalytic activity of the immobilized enzyme may be substantially completely inhibited or, preferably, substantially comparable to the activity of the free enzyme in homogeneous solution. Further, washing of the enzyme-organoclay complex reaction product did not result in any enzyme removal.

Also provided in accordance with the present invention are immobilized enzyme compositions comprising enzyme-organoclay complexes.

It has been discovered that the pH activity profile of the bound enzymes has its maximum very near that of the free enzymes. Further, little or no differences have been found in activity or selectivity between the free and bound enzymes.

There is also provided, in accordance with the present invention, a method for the purification or separation of enzymes and protein mixtures which comprises admixing an organoclay of desired nature with an enzyme containing mixture and recovering the enzyme-organoclay complex reaction product.

DETAILED DESCRIPTION OF THE PREFERRED EMBODIMENTS

In accordance with the present invention, there are provided novel immobilized enzyme compositions comprising enzyme-organoclay complexes which are substantially pH independent and wherein the catalytic activity of the immobilized enzymes may be substantially comparable to the activity of the free enzyme in a homogeneous solution.

The enzymes to which the present invention is applicable for preparing the novel immobilized enzyme compositions of the invention can be any enzyme known in the art.

Enzymes are catalysts elaborated by living organisms that control the many processes associated with life. Many have high specificity with respect to the substances (substrates) whose reactions they catalyze; hence they are usually named by addition of the suffix "ase" to the root of the name of the substrate. They are all proteins, although some contain a nonproteinoid prosthetic group essential for activity.

Enzymes fall into two broad divisions: hydrolases, which control hydrolysis (and resynthesis) of esters, carbohydrates, proteins, amides; and enzymes that control various oxidation-reduction reactions. Almost all enzymes show stereochemical specificity. A few, such as urease, have absolute specificity in that they control the reaction of only one substrate. Certain enzymes show only linkage specificity; for example, there are esterases capable of promoting hydrolysis of any ester regardless of the structures of the acid and alcohol components. The more usual requirements fall in between the absolute and the linkage type, that is, the enzyme requires a specific linkage and also that certain functional groups be in the vicinity of this linkage. It has been found that various proteinases have definite requirements in order to catalyze hydrolysis of peptide bonds. A majority of proteolytic enzymes such as pepsin and trypsin are endopeptidesis which attack centrally located peptide bonds; while some such as carboxypeptides, affect only terminal peptide bonds.

Oxidative enzymes include enzymes known as oxidases that effect oxidation by transfer of hydrogen from the substrate directly to oxygen. Others, known as dehydrogenases, transfer hydrogen not to oxygen but to an acceptor or coenzyme. Enzymes that fall into this group include, for example, tyrosinase (oxidases); yellow enzyme of yeast (dehydrogenases) hemoglobin, catalase and peroxidase (oxidases).

A more limited number of enzymes such as carboxylase, catalase and peroxidase control processes other than hydrolysis and oxidation-reduction.

All of the above enzymes and the many more that are known, are being isolated and identified and/or are being synthesized are believed applicable for use in accordance with the practice of the present invention.

As indicated, organic-clay complexes (organoclays) are well known in the art as exemplified by the aforementioned patents, the entire disclosures of which are incorporated herein by reference. As used in the present specification and in the appended claims, the term "organoclay" refers to various clay types, e.g. smectites, that have organo ammonium ions and/or organometallic cations substituted for cations between the clay layers. The term "organo ammonium ions" as used in the present specification and in the appended claims refers to all onium ions containing alkyl or aryl groups and substituted alkyl and aryl groups and related phosphonium, arsonium, sulfonium and the like compounds.

The clay substrates which are applicable for use in this invention are those which exhibit substantial base-exchange properties, and particularly those exhibiting comparatively high base-exchange properties and containing cations capable of more or less easy replacement. The preferred clay minerals are the smectite type clays; particularly the smectite clays which have a cation exchange capacity of at least about 60 milli-equivalents per 100 grams of clay. Suitable clays include the naturally occurring Wyoming variety of swelling bentonite or montmorillonite and similar clays, and hectorite, which is a swelling type magnesium-lithium silicate clay. These clays are, preferably, converted to the sodium form if they are not already in this form. This can be effected by a cation exchange reaction with a soluble sodium compound in a manner well known in the art. Also suitable are smectite type clays prepared synthetically such as montmorillonite, beidellite, hectorite, saponite, nontronite and stevensite, and 2:1 clay materials such as vermiculites.

The organoclays useful in this invention include those set forth in U.S. Patent No. 2,531,427 to Hauser which are the reaction products of a clay of the character described and an organic compound, more particularly one generally defined and referred to as an "onium" compound.

A great number of such organic compounds are capable of reacting with clays, particularly smectites. These compounds may include salts of aliphatic, cyclic, aromatic, and heterocyclic amines, primary, secondary and tertiary amines and polyamines, also quaternary ammonium compounds, as well as other monovalent or polyvalent onium compounds such as triphenylallyl phosphonium and arsonium halides, or dialkyl or aryl sulphonium and selenonium halides. In general, in addition to being capable of reacting with the smectite clay materials in the manner known in the art, the organic groups to be used are preferably hydrophobic rather than hydrophillic in nature and the organoclays are modified clays having an organophillic surface which exhibit in organic liquids, some of those characteristics which untreated clays exhibit in water. For example, they typically will swell in many organic liquids and will form stable gels and colloidal dispersions.

Also suitable for use in preparing the organoclays are organometallic cations containing organo groups such as bipyridyl, orthophenanthrolein, arene or alkyl liquids which includes, for example, $[Fe(2,2'-bipyridyl)_3]^{2+}$ cations.

Particularly useful in this invention are organoclays where a quaternary ammonium salt has been substituted onto the clay.

Generally, the quaternary ammonium salt substituted onto the clay has organic groups which will range from aliphatic hydrocarbons of from 1 to 24 or more carbons, to substituted alkyl chains such as those containing functional groups, branching side chains and aromatic side chains, to aromatic organic molecules, such as phenyl, substituted phenyls and benzyl groups that could have a host of groups substituted on the benzyl ring. The number of benzyl versus straight chain hydrocarbons substituted on the ammonium ion can vary from 3 to 0 (i.e. dimethyl dioctododecyl, methyl benzyl dioctododecyl, dibenzyl dioctobenzyl, tribenzyl octadecyl, methyl dibenzyl octodecyl). The amount of alkyl ammonium salt substituted on the clay can vary between 0.5% to 100% or more of the cation exchange capacities.

In particular the preferred organoclay used in this invention comprises one or more of the following quaternary ammonium cation modified montmorillonite clays:

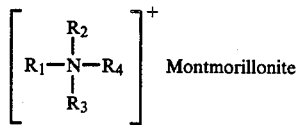

wherein $R_1$ is an alkyl group having at least one carbon but, more typically, at least 10 carbon atoms and up to, for example, 24 carbon atoms or more, and preferably, having a chain length of from 12 to 18 carbon atoms; $R_2$ is hydrogen, a lower alkyl group of from 1 to 4 carbon atoms, benzyl, an alkyl group of at least 10 carbon atoms and up to, for example, 24 carbon atoms or more, and preferably from 12 to 18 carbon atoms or phenyl, substituted phenyl or related aromatic groups; and $R_3$ and $R_4$ are each hydrogen or lower alkyl groups, viz., they contain carbon chains of from 1 to 4 atoms, and preferably are methyl groups or phenyl, substituted phenyl or related aromatic groups. An organoclay that has been found to be particularly suitable is hexadecyltrimethylammonium bentonite.

Other organoclays utilizable in the invention include benzyl organoclays such as dimethyl benzyl (Hydrogenated tallow) ammonium bentonite; methyl benzyl di (hydrogenated tallow) ammonium bentonite; and more generally quaternary ammonium cation modified montmorillonite clays represented by the formula:

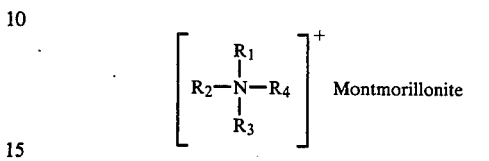

wherein $R_1$ is $CH_3$; substituted alkyl chains such as those containing functional groups, branched side chains and aromatic side chains, $C_6H_5CH_2$ or phenyl; $R_2$ is $C_6H_5CH_2$; and $R_3$ and $R_4$ are alkyl groups containing long chain alkyl groups having typically 14 to 22 carbon atoms, and most preferably wherein 20% to 35% of said long chain alkyl groups contain 16 carbon atoms and 60% to 75% of said long chain alkyl radicals contain 18 carbon atoms.

Also suitable are onium ions of the type

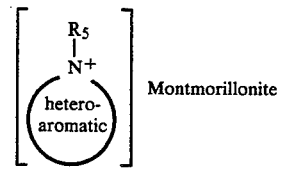

where N is part of a heteroaromatic system such as pyridine, imidazole, triazine, purine, etc. and $R_5$ is hydrogen or an alkyl group having at least one carbon but, more typically, at least 10 carbons and up to, for example, 24 carbon atoms or more, or substituted, or functionalyzed derivatives of these groups.

Other organoclays applicable for use include tris metal chelate cation forms of the type

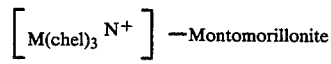

where M is a metal ion, typically a divalent ion like $Fe^{2+}$, $Zn^{2+}$, $Ni^{2+}$ and chel is a bidentate ligand such as bipyridyl, orthophenanthiolein and the like.

In accordance with the present invention, the novel immobilized enzyme composition can be prepared by reacting an admixture of an enzyme, preferably in the form of an aqueous solution thereof, with an aqueous dispersion of an organoclay. Preferably, all reactions are carried out in a buffer solution containing, for example 0.1M $NaH_2PO_4$. The buffer solution could be adjusted to the optimum pH of the enzyme. The enzymeorganoclay complex can then be separated and recovered from the liquid reaction mixture by any well-known means, such as centri- fuging.

The amount of enzyme and organoclay reactants used in preparing the enzyme-organoclay complexes of the invention is not critical, and in general, up to about a 1:1 mixture by weight of enzyme to organoclay can be used. The organoclays have been found to be capable of binding up to about 40 weight percent of enzyme, thus, a large excess of enzyme should, in general, be avoided for economic considerations.

The reaction can be carried out at ambient conditions by simply stirring the mixture of reactants, though temperatures from about the freezing point of water to about 30° C. or even higher may be used.

The enzyme-organoclay complexes of the present invention have high resistance to denaturation with water or the like and the immobilization is substantially independent of the pH of the reaction mixture or of the pH of the enzymatic reaction-system.

Having generally described this invention, a further understanding can be obtained by reference to certain specific examples which are provided herein for purposes of illustration only and are not intended to be limiting unless otherwise specified.

EXAMPLE 1

A natural sodium smectite from a Wyoming bentonite was used in the experiments of this Example. The clay was dispersed in water and the $<2\mu$ fraction was collected by sedimentation methods. This suspension was treated with hexadecyltrimethylammonium (HDTMA) bromide in concentrations several times the cation exchange capacity of the smectite (0.92 meq/g) in order to place the HDTMA cations on the exchange complex. After several hours equilibration, the complex was filtered and washed with distilled water to remove excess organic salt. The washed HDTMA-smectite complex was frozen and freeze-dried then stored in stoppered bottles until used.

Urease Type IV from jack beans purchased from Sigma Chemical Co. was used in the experiments of this Example. This enzyme had an activity of 50,000 $\mu M$ units/gram. All enzymatic reactions were carried out in a buffer solution containing 0.1M $NaH_2PO_4$. The buffer solution was adjusted to pH 7.0 with NaOH. For the pH study, the phosphate buffer was adjusted to the appropriate pH values using either HCl or NaOH.

Enzyme Immobilization

For most experiments, urease type IV was immobilized on HDTMA-smectite at the 1% (w/w) level. A urease solution containing 1 mg urease/ml buffer was prepared fresh before each experiment. One milliliter of the enzyme solution was added to 100 mg HDTMA-smectite contained in 4 ml of buffer. The enzyme-clay mixture was then shaken gently for 18-20 hours at 20° C. For comparison, 1 ml of the enzyme solution was also added to 4 ml buffer without HDTMA-smectite (referred to as "free enzyme") and treated in the same fashion. Various amounts of the clay-enzyme complex and free enzyme were prepared according to the above proportions depending on the number of assays to be performed. Urease activity was also evaluated at the 2% and 4% (w/w) levels by preparing urease solutions containing 2 and 4 mg urease/ml of buffer. To determine the absorption capacity of the HDTMA-smectite, urease was added directly as a powder to 100 mg of HDTMA-clay contained in 5 ml buffer in the following amounts: 0.010 g (10%); 0.015 g (15%); 0.020 g (20%); 0.030 g (30%); 0.040 g (40%); 0.050 g (50%); 0.075 g (75%). In all experiments, the degree of immobilization was determined by separating the solid and liquid phases and comparing activity in the liquid phase (supernatant) to the activity of the clay-enzyme suspension. Separation of the liquid phase was accomplished by centrifuging at 10,000 RPM for 20 minutes.

Enzyme Assay

Enzymatic reactions were initiated by adding 1 ml of either the free or immobilized-urease (organoclay-enzyme complex) to 39 ml of buffer solution containing various amounts of urea. The organoclay-enzyme complex suspension was stirred continuously on a magnetic stirrer while dispensing the 1 ml aliquots. The assay solutions were contained in glass bottles which were shaken vigorously after addition of the enzyme. A drop of toluene was added to the assay solution to prohibit microbial growth. For the Michaelis-Menten studies, the amount of urea was varied from 0.1 to 1 mmoles. All other experiments were carried out using 1 mmole urea. Several alternate substrates were also assayed. These were: benzamide, hydroxyurea, acetamide, thiourea, semicarbazide, glutamine and asparagine. Ammonia produced from 1 mmole substrate after 24 hours was determined for free and immobilized urease at the 4% (w/w) level. For the rate studies, individual bottles were assayed after a given reaction time. All measurements were performed at 20° C. in duplicate.

Analyses for $NH_3$ formation were made with an Orion ammonia electrode Model 95-10. Standardization of the electrode with $NH_4Cl$ solutions was performed at the beginning of each experiment.

It was determined that at a 1% (w/w) loading level of enzyme, there was no significant difference in the rate of $NH_3$ production between free enzyme and the enzyme-organoclay complex. In addition, the rate of $NH_3$ production for different loadings of enzyme on the enzyme-organoclay complex of this Example was determined to be 1% (w/w): $7.63 \times 10^{-5}$ mmoles/sec.
2% (w/w): $15.97 \times 10^{-5}$ mmoles/sec.
4% (w/w): $30.55 \times 10^{-5}$ mmoles/sec.

It was determined that the Michaelis-Menten parameters Km and V max were identical for the free enzyme and the enzyme-organoclay complex.

It was also determined by an evaluation of the absorption capacity of the organoclay complex of this Example that as much as 40% by weight of enzyme can be bound to the organoclay complex before an appreciable amount of enzyme remains in solution in the liquid phase. Washing experiments run on an enzyme-organoclay complex of this Example which contained 10 percent by weight of enzyme showed no enzyme activity in the washings whereas the enzyme-organoclay complex was extremely active.

In an evaluation of the pH profile of the enzyme-organoclay complex of this Example, in comparison with the pH profile of the free enzyme in solution, over a pH range of from 5 to 8, there was no apparent difference in the position of the maximum activity between the enzyme-organoclay complex of this Example and the free enzyme. The enzyme-organoclay complex appeared to be more active in the pH range of 5.5 to 7.0 than was the free enzyme.

In the experiments run using substrates other than urea, no difference in selectivity between the free enzyme and the enzyme-organoclay complex of this Example was observed.

Thermal stability of the immobilized enzyme of this Example was compared with the free enzyme after heating at 20° C., 37° C. or 50° C. for 18 hours. The clay-enzyme preparations and free enzymes were then assayed for activity. It was determined that the activity of the immobilized enzyme was reduced a significantly greater amount than that of the free enzyme after heating at 37° C. and 50° C., but the immobilized enzyme still exhibited some activity after heating at 50° C.

EXAMPLE 2

Using the procedure of Example 1, and the Wyoming bentonite used in the experiments of Example 1, organoclay complexes are prepared with hexadecyltrimethylammonium (HDTMA) bromide, hexadecylpyridinum (HDPy) bromide and [Fe(2',2'-bipyridyl)$_3$]Cl$_2$.

The urease type IV (jack bean) enzyme of Example 1 is immobilized on each of the three organoclay complexes of this Example at the 1% (w/w) level using the enzyme immobilization procedure of Example 1.

Using the enzyme assay method of Example 1, the activity of the immobilized enzymes on the three different organoclay complexes of this Example are evaluated in comparison with the activity of the free enzyme.

In Table I, below is reported the activity of the immobilized enzymes of this Example

TABLE I

| Organic Cation on Organoclay Complex | Urease Activity (mmoles NH$_3$ in 80 min) |
|---|---|
| Free Enzyme | 0.36 |
| HDTMA | 0.172 |
| [Fe(bipy)$_3$]$^{2+}$ | 0.144 |
| HDPy | 0.35 |

EXAMPLE 3

A natural sodium smectite (montmorillonite) from a Wyoming bentonite is converted to the hexadecyltrimethylammonium ammonium (HDTMA$^+$) exchanged form of montmorillonite as described in Example 1, for use in this Example. A sodium exchanged form of the montmorillonite is also prepared for use in comparison experiments in this Example.

Glucose oxidase, A. niger (EC 1.1.3.4), with an activity of 111 IUB units/mg, obtained from Aldrich Chemical Company, Inc., is the enzyme used in the experiments of this Example.

Enzyme immobilization is carried out by adding the desired amount of enzyme to buffered suspensions (pH 4.00) of the organoclay (HDTMA+) complex of this Example and to the sodium exchanged montmorillonite, at 20° C. The buffered suspensions also contained 3 drops of toluene per liter of composition to inhibit bacterial contaminants.

Enzyme activity is measured polarographically using a Model XXI Sargent Polarograph equipped with a calibrated Clark oxygen electrode (Model 5331, Yellow Springs Instrument Company). A thermostatted glass reaction vessel with a volume of 57.7 ml filled with a solution containing 0.1 M beta-D (+)-glucose (Aldrich Chemical Company) and 0.2M buffer is saturated with oxygen. The desired amount of enzyme is injected through a side port with vigorous agitation.

pH profile studies are carried out by injecting a small aliquot of immobilized enzyme of this Example (enzyme on HDTMA+montmorillonite) at pH 4.00 into the reaction vessel filled with freshly oxygenated 0.1M glucose at the desired buffered pH. Substrate solutions in the pH range of 3.00 to 8.00 are prepared using acetate (pH 3.00 to 5.00) or phosphate (pH 6.00 to 8.00) buffers. The immobilized enzyme samples typically contain 20.0 mg clay and 200 μg of bound enzyme. Samples of free enzymes are also evaluated in the same manner.

For comparison, pH profile studies of active enzyme immobilized on sodium-montmorillonite are determined at different values of substrate solution pH by immobilizing the enzyme (1.0 weight percent) at pH 4.0 and then injecting the sample in the reaction vessel buffered at the desired pH in the range of 3.0 to 8.0. Immediately following each assay, the contents of the vessel are centrifuged, and the supernatant is reoxygenated and assayed for activity. Any desorbed enzyme detected in the second assay is presumed to have been present as free enzyme in the first assay, and to have exhibited the same activity in both determinations.

Glucose oxidase at pH 4.0 is immobilized completely on the organoclay complex of this Example and on the sodiummontmorillonite clay at the 1 weight percent level. Polarographically-determined O$_2$ uptake for the oxidation of 0.1 glucose at pH 4.0 and 20° C. by 200 μg of free enzyme and by the same amount of immobilized enzyme of this Example (1 weight percent) shows that approximately 50% of the enzyme activity is retained by the immobilized enzyme of this Example in comparison to the activity of the free enzyme. Using the same test procedure, only 10% of the enzyme immobilized on sodium-montmorillonite is found to be active.

It is also determined that the immobilized glucose oxidase of this Example exhibited no desorption over the pH range of 3.0 to 8.0 and the cationic, neutral and anionic forms of the enzyme all remain bound to the organoclay complex after extensive washing.

In comparison, a large fraction of the active enzyme immobilized sodium-montmorillonite is desorbed at pH values above approximately 4.0. In addition, all physically-absorbed active enzyme could be removed by washing the clay several times with buffer solution at a pH of 7.0.

Having now fully described the invention, it will be apparent to one of ordinary skill in the art that many changes and modifications can be made thereto without departing from the spirit or scope of the invention as set forth herein. The described embodiments are to be considered in all respects only as illustrative and not restrictive and the scope of the invention is, therefore, indicated by the appended claims rather than by the foregoing description. All claims that come within the meaning and range of equivalency of the claims are to be embraced within this scope.

What is claimed is:

1. A method for preparing immobilized enzymes which comprises reacting an enzyme to be immobilized with an organoclay comprising a clay selected from the group consisting of smectite type clays, hectorite and vermiculite, at least some cations of which have been replaced by onium ions and/or organometallic cations to render the clay hydrophobic.

2. The method according to claim 1 wherein the reaction is carried out in an aqueous medium.

3. The method according to claim 1 wherein an aqueous solution of said enzyme is admixed with an aqueous dispersion of said organoclay.

4. The method according to claim 3 wherein said enzyme solution contains a buffer and said organoclay dispersion is buffered.

5. The method according to claim 1 wherein said organoclay comprises a hydrophobic-modified smectite clay.

6. The method according to claim 1 wherein said organoclay comprises an enzyophyllic onium smectite clay.

7. The method according to claim 1 wherein said organoclay comprises an organophillic ammonium montmorillonite clay.

8. Immobilized enzyme compositions comprising enzyme organoclay complexes, the organoclay used comprising a clay selected from the group consisting of smectite type clays, hectorite and vermiculite, at least some cations of which have been replaced by onium ions and/or organometallic cations to render the clay hydrophobic.

9. The immobilized enzyme composition according to claim 8 wherein said organoclay comprises a hydrophobic-modified smectite clay.

10. The immobilized enzyme composition according to claim 8 wherein said organoclay comprises an organophillic onium smectite clay.

11. The immobilized enzyme composition according to claim 8 wherein said organoclay comprises an organophillic ammonium montmorillonite clay.

12. The immobilized enzyme composition according to claim 8 wherein said enzyme is glucose oxidase or urease.

13. The immobilized enzyme composition according to claim 8 wherein said enzyme-organoclay complex comprises up to a 40 weight percent of said enzyme based on the weight of said organoclay.

14. A method for purification or separating of enzymes and protein mixtures which comprises admixing an organoclay comprising a clay selected from the group consisting of smectite type clays, hectorite and vermiculite, at least some cations of which have been replaced by onium ions and/or organometallic cations, which an enzyme-containing omposition and recovering the enzyme-organoclay complex reaction product.

* * * * *